(12) United States Patent
Weaver

(10) Patent No.: US 9,211,346 B2
(45) Date of Patent: Dec. 15, 2015

(54) CARRIER-LINKED MAGNETIC NANOPARTICLE DRUG DELIVERY COMPOSITION AND METHOD OF USE

(75) Inventor: John B. Weaver, Hanover, NH (US)

(73) Assignee: TRUSTEES OF DARTMOUTH COLLEGE, Hanover, NH (US)

(*) Notice: Subject to any disclaimer, the term of this patent is extended or adjusted under 35 U.S.C. 154(b) by 0 days.

(21) Appl. No.: 13/993,359

(22) PCT Filed: Dec. 1, 2011

(86) PCT No.: PCT/US2011/062769
§ 371 (c)(1),
(2), (4) Date: Jul. 22, 2013

(87) PCT Pub. No.: WO2012/082382
PCT Pub. Date: Jun. 21, 2012

(65) Prior Publication Data
US 2013/0302408 A1 Nov. 14, 2013

Related U.S. Application Data

(60) Provisional application No. 61/422,285, filed on Dec. 13, 2010.

(51) Int. Cl.
| | |
|---|---|
| *A61K 9/14* | (2006.01) |
| *A61K 47/48* | (2006.01) |
| *A61K 9/00* | (2006.01) |
| *A61K 41/00* | (2006.01) |
| *B82Y 5/00* | (2011.01) |
| *B82Y 25/00* | (2011.01) |
| *A61K 9/127* | (2006.01) |
| *A61M 37/00* | (2006.01) |

(52) U.S. Cl.
CPC ......... *A61K 47/48815* (2013.01); *A61K 9/0009* (2013.01); *A61K 9/1271* (2013.01); *A61K 41/00* (2013.01); *A61K 41/0028* (2013.01); *A61K 47/48861* (2013.01); *A61K 47/48884* (2013.01); *B82Y 5/00* (2013.01); *B82Y 25/00* (2013.01); *A61M 37/00* (2013.01); *Y10S 977/773* (2013.01); *Y10S 977/906* (2013.01); *Y10S 977/907* (2013.01)

(58) Field of Classification Search
None
See application file for complete search history.

(56) References Cited

U.S. PATENT DOCUMENTS

| | | | |
|---|---|---|---|
| 4,603,044 A | 7/1986 | Geho et al. | 424/450 |
| 4,957,773 A | 9/1990 | Spencer et al. | 427/570 |
| 5,958,412 A | 9/1999 | Welt et al. | 424/178.1 |
| 2003/0211045 A1* | 11/2003 | Leszcyznska et al. | 424/9.321 |
| 2004/0229295 A1 | 11/2004 | Marchitto et al. | 435/7.5 |
| 2005/0042753 A1 | 2/2005 | Yang et al. | 435/455 |

(Continued)

OTHER PUBLICATIONS

L Chen, DJ Waxman. "Intratumoral Activation and Enhanced Chemotherapeutic Effect of Oxazaphosphorines following Cytochrome P-450 Gene Transfer: Development of a Combined Chemotherapy/Cancer Gene Therapy Strategy". Cancer Research, vol. 55, Feb. 1, 1995, pp. 581-589.*

(Continued)

*Primary Examiner* — Isaac Shomer
(74) *Attorney, Agent, or Firm* — Licata & Tyrrell P.C.

(57) ABSTRACT

The present invention is a targeted drug delivery composition composed of carrier-linked magnetic nanoparticles. Using an alternating magnetic field, nanoparticles bound to a targeted cell are selectively ruptured thereby releasing therapeutic agents at the desired site of action.

7 Claims, 1 Drawing Sheet

(56) References Cited

U.S. PATENT DOCUMENTS

| | | | |
|---|---|---|---|
| 2005/0090732 A1* | 4/2005 | Ivkov et al. | 600/411 |
| 2007/0292495 A1 | 12/2007 | Ludwig et al. | 424/450 |
| 2009/0246142 A1 | 10/2009 | Bhatia et al. | 514/1.1 |

OTHER PUBLICATIONS

M Yanase, M Shinkai, H Honda, T Wakabayashi, J Yoshida, T Kobayashi. "Intracellular Hyperthermia for Cancer Using Magnetite Cationic Liposomes: An in vivo Study." Japan Journal of Cancer Research, vol. 89, Apr. 1998, pp. 463-470.*

M Morille, C Passirani, A Vonarbourg, A Calvreul, JP Benoit. "Progress in developing cationic vectors for non-viral systemic gene therapy against cancer." Biomaterials, vol. 29, 2008, pp. 3477-3496.*

ML Immordino, F Dosio, L Cattel. "Stealth liposomes: review of the basic science, rationale, and clinical applications, existing and potential." International Journal of Nanomedicine, vol. 1(3), 2006, pp. 297-315.*

G Baldi, G Lorenzi, C Ravagli. "Hyperthermic effect of magnetic nanoparticles under electromagnetic field." Processing and Application of Ceramics, vol. 3 [1-2], 2009, pp. 103-109.*

Bakina, E. And Farquhar, D. "Intensely Cytotoxic Anthracycline Prodrugs: Galactosides" Anti-cancer Drug Design 1999 14:507-515.

Bridgewater et al. "The Bystander Effect of the Nitroreductase/CB1954 Enzyme/Prodrug System Is Due to a Cell-Permeable Metabolite" Human Gene Therapy 1997 8:709-717.

Chen et al. "Potentiation of Cytochrome P450/Cyclophosphamide-based Cancer Gene Therapy by Coexpression of the P450 Reductase Gene" Cancer Research 1997 57:4830-4837.

Danks et al. "Comparison of Activation of CPT-11 by Rabbit and Human Carboxylesterases for Use in Enzyme/Prodrug Therapy" Clinical Cancer Research 1999 5:917-924.

Evrard et al. "Increased Cytotoxicity and Bystander Effect of 5-fluorouracil and 5'-deoxy-5-fluorouridine in Human Colorectal Cancer Cells Transfected with Thymidine Phosphorylase" British Journal of Cancer 1999 80(11):1726-1733.

Friedlos et al. "Mustard Prodrugs for Activation by *Escherichia coli* Nitroreductase in Gene-directed Enzyme Prodrug Therapy" Journal of Medicinal Chemistry 1997 40:1270-1275.

Hamstra, D.A. and Rehemtulla, A. "Toward an Enzyme/Prodrug Strategy for Cancer Gene Therapy: Endogenous Activation of Carboxypeptidase A Mutants by the PACE/Furin Family of Propeptidases" Human Gene Therapy 1999 10:235-248.

Malamitsi et al. "Intracavitary Use of Two Radiolabeled Tumor-associated Monoclonal Antibodies" The Journal of Nuclear Medicine 1988 29:1910-1915.

Mullen et al. "Transfer of the Bacterial Gene for Cytosine Deaminase to Mammalian Cells Confers Lethal Sensitivity to 5-fluorocytosine: A Negative Selection System" Proceedings of the National Academy of Science USA 1992 89:33-37.

Rainov et al. "New Prodrug Activation Gene Therapy for Cancer Using Cytochrome P450 4B1 and 2-Aminoanthracene/4-Ipomeanol" Human Gene Therapy 1998 9:1261-1273.

Sharkey et al. "A Universal Pretargeting System for Cancer Detection and Therapy Using Bispecific Antibody" Cancer Research 2003 63:354-363.

Stancovski et al. "Molecular and Clinical Aspects of the Neu/ErbB-2 Receptor Tyrosine Kinase" *Mammary Tumorigenesis and Malignant Progression* Ed: R. Dickson and M. Lippman. Washington DC: Kluwer Academic Publishers, 1994 161-191.

Vandier et al. "Transactivation of the Metallothionein Promoter in Cisplatin-resistant Cancer Cells: A Specific Gene Therapy Strategy" Journal of the National Cancer Institute 2000 92:642-647.

Verstijnen et al. "CEA-specificity of CEA-reactive Monoclonal Antibodies. Immunochemical and Immunocytochemical Studies" Anticancer Research 1986 6(1):97-104 (Pubmed Abstract Only).

Weyel et al. "Secreted Human β-Glucuronidase: A Novel Tool for Gene-directed Enzyme Prodrug Therapy" Gene Therapy 2000 7:224-231.

Yamanaka et al. "Overexpression of HER2/*neu* Oncogene in Human Pancreatic Carcinoma" Human Pathology 1993 24:1127-1134.

International Search Report from PCT/US2011/62769, Apr. 3, 2012, PCT.

International Preliminary Report on Patentability issued in corresponding PCT application No. PCT/US2011/62769, Jun. 27, 2013, PCT.

* cited by examiner

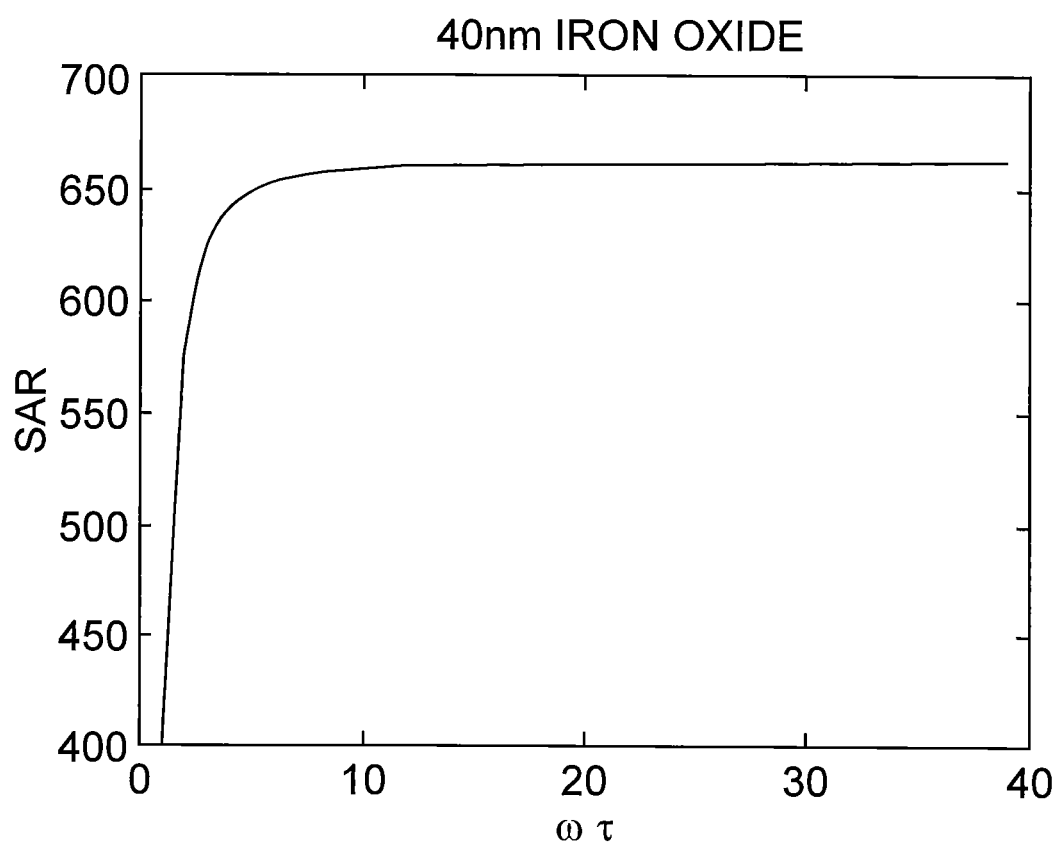

CARRIER-LINKED MAGNETIC NANOPARTICLE DRUG DELIVERY COMPOSITION AND METHOD OF USE

The patent application is the national phase under 35 U.S.C. §371 of PCT International Application No. PCT/US2011/062769, filed Dec. 1, 2011, which claims the benefit of priority from U.S. Provisional Application Ser. No. 61/422,285 filed Dec. 13, 2010, the contents of which are incorporated herein by reference in their entireties.

BACKGROUND OF THE INVENTION

Magnetic nanoparticles are particles composed of ferrite (e.g., $Fe_3O_4$ and $Fe_2O_3$) and have been suggested for use in delivering drugs or physiologically active materials with or without coatings such as dextran, lipid, liposome, polymer or the like (JP 2002-128523; JP 9-110722; U.S. Pat. No. 7,560,097; U.S. Pat. No. 7,731,648). However, the use of magnetic nanoparticles in the medical field relies on maintaining a physiologically active material within the nanoparticles and selective delivery to an intended site (targeting capability).

SUMMARY OF THE INVENTION

The present invention features a composition, kit and method for delivering therapeutic agents. The composition of the invention is composed of (a) a first carrier-linked magnetic nanoparticle containing a prodrug; and (b) a second carrier-linked magnetic nanoparticle containing a moiety for activating the prodrug, wherein one or both of the carrier-linked magnetic nanoparticles of (a) and (b) comprises a targeting moiety. In one embodiment, the first or second carrier is a liposome.

The method of the present invention involves administering to a subject in need thereof a carrier-linked magnetic nanoparticle containing a therapeutic agent and applying an alternating magnetic field to the subject thereby providing the therapeutic agent to the subject.

BRIEF DESCRIPTION OF THE DRAWINGS

FIG. 1 shows the specific absorption rate (SAR) versus the product of frequency and relaxation time of magnetic nanoparticles, wherein the SAR to the left is low and the SAR to the right it is much higher.

DETAILED DESCRIPTION OF THE INVENTION

The present invention features a drug delivery composition or system composed of carrier-linked magnetic nanoparticles (also referred to herein as nanoparticles). In one embodiment, the composition contains two carrier-linked magnetic nanoparticles: one nanoparticle containing a therapeutic prodrug and the other nanoparticle containing an activator of the prodrug. In another embodiment, the composition is a nanoparticle containing an active therapeutic agent. When an alternating magnetic field (AMF) is applied to the carrier-linked magnetic nanoparticles, the drug of interest is delivered locally to targeted cells. It is contemplated that either heat or mechanical action of the AMF on the carrier-linked magnetic nanoparticles facilitates release of the therapeutic agent, or prodrug and activator. The distinction between heat and mechanical action is blurred at those size scales.

In one embodiment, the carrier is a drug carrying nanoparticle. In another embodiment of the present invention, the carrier is a liposome. In accordance with these embodiments, the magnetic nanoparticle is said to be "carrier-linked" in that the magnetic nanoparticle is encapsulated within or otherwise associated with (e.g., outside) the carrier.

An advantage of using liposomes is that the liposomes are ruptured only when bound to the targeted cells, whereas unbound liposomes would remain intact. The mechanism is the "relaxation time," $\tau$. Bound nanoparticles have now been found to possess longer relaxation times. When analyzing the simulation of specific absorption rate (SAR) versus the product of frequency and relaxation time, there is a shoulder (FIG. 1). To the left, the SAR is low and to the right it is much higher. Therefore, when applying an AMF, a frequency is selected where the unbound liposomes would have a very low SAR and the bound liposomes would have a very high SAR. The low SAR would not be sufficient to rupture the liposomes, whereas the higher SAR would be sufficient to rupture the liposomes.

For the purposes of the present invention, a "magnetic nanoparticle" refers to a nanoparticle that can be manipulated using a magnetic field. Magnetic nanoparticles of the present invention can be composed of one or more magnetic elements such as iron, nickel, and cobalt as well as mixtures, composites, oxides or alloys thereof. Exemplary metals and alloys of use include Au, Ag, Pt, Cu, Gd, Zn, Fe, Co, Au/Fe, Au/Cu, Au/Gd, Au/Zn, Au/Fe/Cu, Au/Fe/Gd, Au/Fe/Cu/Gd, and the like. In particular embodiment, the nanoparticle of the invention has as a main component, any one of magnetite, $Fe_2O_3$, $Fe_3O_4$, mixed ferrite, or other iron-containing compounds including organic ferromagnetic material. Nanoparticles of the present invention can be synthesized using any conventional method which allows for capture of a therapeutic agent in the core.

The mean diameter of the present nanoparticle is generally between 0.5 and 500 nm, more desirably between 1 and 100 nm, and most desirably between 1 and 50 nm or 1 and 20 nm. The mean diameter can be measured using techniques well-known in the art such as transmission electron microscopy (TEM).

As used herein the term "prodrug" refers to a pharmacologically inactive derivative of a parent drug molecule that requires biotransformation within the organism to release the active drug. Preferred prodrugs are variations or derivatives of the compounds that have groups cleavable under by a particular activator moiety (e.g., an enzyme). For example, prodrugs become pharmaceutically active in vivo when they undergo enzymatic degradation or other biochemical transformation (e.g., phosphorylation, hydrogenation, dehydrogenation, glycosylation, etc). Prodrugs often offer advantages of solubility, tissue compatibility, or delayed release in the mammalian organism. See, e.g., Bundgard (1985) *Design of Prodrugs*, pp. 7-9, 21-24, Elsevier, Amsterdam; Silverman (1992) *The Organic Chemistry of Drug Design and Drug Action*, pp. 352-401, Academic Press, San Diego, Calif. Common prodrugs include acid derivatives such as, esters prepared by reaction of parent acids with a suitable alcohol, amides prepared by reaction of the parent acid compound with an amine, or basic groups reacted to form an acylated base derivative. Examples of prodrugs and their respective activation moieties that can be incorporated into the nanoparticles of the instant invention include, but are not limited to HMR 1826 activated by β-glucuronidase (Weyel, et al. (2000) *Gene Ther.* 7:224-231), CB1954 (5-(aziridin-1-yl)-2,4-dinitrobenzamide) activated by nitroreductase (Friedlos, et al. (1997) *J. Med. Chem.* 40:1270-1275; Bridgewater, et al. (1997) *Hum. Gene Ther.* 8:709-717), methotrexate-α-peptide activated by carboxypeptidase (Hamstra & Rehemtulla (1999) *Hum. Gene Ther.* 10:235-248), cyclophosphamide activated by CYP2B1 and p450 reductase (Chen, et al. (1997) *Cancer Res.* 57:4830-4837), 2-aminoanthracene or 4-ipomennol activated by CYP4B1 (Rainov, et al. (1998) *Hum. Gene Ther.* 9:1261-1273), 5-fluorouracil or 5'-deoxy-5-fluorouridine activated by thymidine phosphorylase (Evrard, et al. (1999) *Br. J. Cancer* 80:1726-1733), irinotecan activated by carboxylesterase (Danks, et al. (1999) *Clin. Cancer Res.* 5:917-924), anthracycline activated by β-galactosidase (Bakina & Farquhar (1999) *Anticancer Drug Des.* 14:507-515), 5-fluorocytosine activated by cytosine deaminase (Mullen, et al. (1992) *Proc. Natl. Acad. Sci. USA* 89:33-37) and ganciclovir activated by thymidine kinase (Vandier, et al. (2000) *J. Natl. Cancer Inst.* (Bethesda) 92:642-647).

As used herein, the term "therapeutic agent" refers to any compound or molecule that is used for the treatment or prevention of a disease or for improving the well being of a mammal. Examples of therapeutic agents include, but are not limited to, anti-neoplastic therapeutic agents, anti-inflammatory compounds, narcotics, depressants, anti-depressants, stimulants, hallucinogens, analgesics, antibiotics, antipyretics, vasodilators, anti-angiogenics, cytovascular agents, signal transduction inhibitors, vasoconstrictors, hormones, steroids, antibodies, radioisotopes, small-interfering RNAs (siRNAs), and prodrugs (e.g., as described herein). In particular embodiments, the therapeutic agent is an anti-neoplastic agent such as an alkaloidl; podophyllin or podophyllotoxin, and derivatives thereof (e.g., etoposide, etoposide phosphate, teniposide, etc.); or camptothecin (e.g., irinotecan, topotecan, etc.); taxane (paclitaxol, etc.).

A carrier-linked magnetic nanoparticle refers to a nanoparticle enclosed within are associated with (covalently or noncovalently) a carrier. In embodiments pertaining to the use of a liposome, the nanoparticle can be enclosed within a lipid membrane or liposome membrane (i.e., liposome-encapsulated), be embedded in the lipid membrane or be associated with the outer surface of the membrane. Association of the magnetic microparticles with a lipid membrane allows the particles to be dispersed in an aqueous medium and makes it feasible to form a magnetic vesicular particle-containing preparation exhibiting superior dispersion stability. Magnetic microparticles exhibiting a relatively high residual magnetism often cause magnetic coagulation, forming precipitates in medium. The lipid membrane is inherently biocompatible and exhibits enhanced affinity to tissue, and specifically, directionality to hydrophobic tissue. The lipid membrane of the liposome is generally a lipid multi-layer membrane, preferably a multi-layer membrane formed of an amphiphilic molecule having a medium or long chain aliphatic acid residue or a medium or long chain alkyl group and a hydrophilic group.

Phospholipid and/or glycolipid are preferably used in the instant liposome. Representative examples of phospholipids include phosphatidylcholine, phosphatidylserine, phosphatidylethanolamine, phosphatidylglycerol, phosphatidylinositol, phosphatidic acid, cardiolipin and sphingomyelin. There are also usable phospholipids derived from plants and animals such as egg yolk or soybeans and their hydrogenation products or hydroxide derivatives, so-called semi-synthetic phospholipids. Fatty acids constituting a phospholipid are not specifically limited, and saturated and unsaturated fatty acids are also of use. Specific examples of neutral phospholipids include dipalmitoylphosphatidylcholine (DPPC), distearoylphosphatidylcholine (DSPC), dimyristoylphosphatidylcholine (DMPC), dioleylphosphatidylcholine (DOPE), dimyristoylphosphatidylethanolamine, dipalmitolphosphatidylethanolamine, and distearoylphosphatidylethanolamine.

In some embodiments, the liposomes exhibit a positive surface charge; in other words, the instant liposomes have a cationic surface. To make the liposome surface charge positive, it is preferred to use, together with the foregoing neutral phospholipid, at least one of a cationic phospholipid, a cationic lipid and a long chain cationic compound compatible with a phospholipid. The cationic surface charge of a liposome membrane enables specific introduction of magnetic nanoparticles contained in the preparation into a negatively charged tumor cell. Examples of cationic phospholipids include eates of phosphatidic acid and aminoalcohol, such as an ester of dipalmotoylphosphatidic acid (DPPA) or distearoylphosphatidic acid, and hydroxyethylenediamine. Examples of cationic lipids usable in the invention include 1,2-dioleoyloxy-3-(trimethylammonium)propane (DOTAP), N,N-dioctadecylamidoglycylspermine (DOGS), dimethyloctadecylammonium bromide (DDAB), N-[1-(2,3-dioleyloxy)propyl]-N,N,N-trimethylammonium chloride (DOTMA), 2,3-dioleyloxy-N-[2(spermine-carboxamido) ethyl]-N,N-dimethyl-1-propaneami-niumtrifluoroacetate (DOSPA) and N-[1-(2,3-dimyristyloxy)propyl]-N,N-dimethyl-N-(2-hydroxyethyl)ammonium bromide (DMRIE). Examples of a long chain cationic compound include at least 10 carbon atoms containing salts such as ammonium salt or phosphonium salt. Examples of glyceroglycolipids include glycerolipids such as digalactosyldiglyceride and digalactosyldiglyceride sulfuric acid ester; sphingoglycolipids such as galactosylceramide, galactosylceramide sulfuric acid ester, lactosylceramide, ganglioside G7, ganglioside G6 and ganglioside G4.

An additional feature of the instant invention is a targeting moiety attached to the carrier-linked magnetic nanoparticles. In particular embodiments, the targeting moiety is attached to the surface of the carrier and deliveries or targets the instant nanoparticles to particular cells of interest (e.g., tumor cells, abnormal or undesirable cells, or cells infected with a pathogen). Targeting moieties include physiological material, such as sugar, glycoprotein, aptamer, antibody, antigen, lectin, cytokine, growth factor, adjustment factor, physiologically active peptide, vitamins (e.g., riboflavin), cell adhesion factor or hormone to direct the carrier-linked magnetic nanoparticles to a target cell of interest (e.g., a tumor cell). See, e.g., U.S. Pat. Nos. 4,957,773 and 4,603,044. The targeting moieties can comprise the entire protein or fragments thereof. By way of illustration, there are a number of known markers expressed on the surface of cancer cells. Examples thereof include MN, HER2, MAGE3, VEGF and CEA. In this respect, antibodies or antibody fragments specific for these cancer cell markers can be linked or conjugated to the instant nanoparticles. Antibodies of use in accordance with the present invention include an antibody (e.g., monoclonal or polyclonal) or antibody fragment which binds to a protein or receptor which is specific to a tumor cell. Preferably, the antibody fragment retains at least a significant portion of the full-length antibody's specific binding ability. Examples of antibody fragments include, but are not limited to, Fab, Fab', F(ab')$_2$, scFv, Fv, dsFv diabody, or Fd fragments. Exemplary tumor-specific antibodies for use in the present invention include an anti-HER-2 antibody (Yamanaka, et al. (1993) *Hum. Pathol.* 24:1127-34; Stancovski, et al. (1994) *Cancer Treat Res.* 71:161-191) for targeting breast cancer cells, an anti-A33 antigen antibody for targeting colon or gastric cancer (U.S. Pat. No. 5,958,412), anti-human carcinoembryonic antigen (CEA) antibody for targeting carcinomas (Verstijnen, et al. (1986) *Anti-Cancer Research* 6:97-104), HMFG2 or H17E2 antibodies for targeting breast cancer (Malamitsi, et al. (1988) *J. Nucl. Med.* 29:1910-1915), and bispecific monoclonal antibodies composed of an anti-histamine-succinyl-glycine Fab' covalently coupled with an Fab' of either an anticarcinoembryonic antigen or an anticolon-specific antigen-p antibody (Sharkey, et al. (2003) *Cancer Res.* 63(2): 354-63).

By conjugating the instant nanoparticles with a targeting moiety that specifically bind to target cells, cells can be specifically targeted using the instant nanoparticles thereby improving the therapeutic ratio. In this respect, antibody-conjugated particles can be delivered specifically to tumor cells so even tumor cells which have moved away from the original tumor site can be targeted for therapy.

To conjugate or link the targeting moiety to the foregoing carrier, one or more functional groups can be employed. For example, in addition to the foregoing lipid, other material may optionally be incorporated as a liposome membrane constituent. Examples thereof include glycols such as ethylene glycol and propylene glycol or sterols such as cholesterol which can be functionalized so that the targeting moiety can be attached. For example, a cholesterol incorporated in the liposome membrane is capable of functioning as an anchor to introduce a polyalkylene oxide group. Additional functional groups which can be incorporated include, but are not limited to, amino groups, oxycarbonylimidazole groups and N-hydroxysuccinimide. In particular embodiments, a PEG-modified liposome can be expected to have an effect of having a hydrophilic tendency, becoming less recognizable from an immune system or increasing blood stability. Functions can be adjusted by changing a length of oxyethylene units of a PEG and its introducing ratio. Polyethylene glycol having 10 to 3500 (preferably, 100 to 2000) oxyethylene units is preferred as PEG. A PEG is preferably contained in an amount of 0.1% to 30% by weight, and more preferably 1% to 15% by weight, based on the lipid constituting the liposome.

For therapeutic applications, the instant nanoparticles can be formulated as pharmaceutical compositions, and administered to subjects in a variety of forms. Thus, the nanoparticles can be used as a medicament for tumor targeting therapies, or for in vivo cell and tissue targeting.

Pharmaceutical compositions for oral administration can be in tablet, capsule, powder or liquid form. A tablet can include a solid carrier such as gelatin or an adjuvant or an inert diluent. Liquid pharmaceutical compositions generally include a liquid carrier such as water, petroleum, animal or vegetable oils, mineral oil or synthetic oil. Physiological saline solution, or glycols such as ethylene glycol, propylene glycol or polyethylene glycol can be included. Such compositions and preparations generally contain at least 0.1 wt % of the compound.

Parenteral administration includes administration by intravenous, cutaneous or subcutaneous, nasal, intramuscular, intraocular, transepithelial, intraperitoneal and topical (including transdermal, dermal, ocular, rectal, nasal, inhalation and aerosol), and rectal systemic routes. For intravenous, cutaneous or subcutaneous injection, or injection at the site of affliction (i.e., intratumoral), the active ingredient will be in the form of a parenterally acceptable aqueous solution which is pyrogen-free and has suitable pH, isotonicity and stability. Those of relevant skill in the art are well able to prepare suitable solutions using, for example, solutions of the compounds or a derivative thereof, e.g., in physiological saline, a dispersion prepared with glycerol, liquid polyethylene glycol or oils.

In addition the pharmaceutical compositions can include one or more of a pharmaceutically acceptable excipient, carrier, buffer, stabilizer, preservative or anti-oxidant or other materials well-known to those skilled in the art. Such materials should be non-toxic and should not interfere with the efficacy of the active ingredient. The precise nature of the carrier or other material may depend on the route of administration, e.g., orally or parenterally.

Liquid pharmaceutical compositions are typically formulated to have a pH between about 3.0 and 9.0, wherein the pH of a composition can be maintained by the use of a buffer such as acetate, citrate, phosphate, succinate, Tris or histidine, typically employed in the range from about 1 mM to 50 mM. The pH of compositions can otherwise be adjusted by using physiologically acceptable acids or bases.

Preservatives are generally included in pharmaceutical compositions to retard microbial growth, extending the shelf-life of the compositions and allowing multiple use packaging. Examples of preservatives include phenol, meta-cresol, benzyl alcohol, para-hydroxybenzoic acid and its esters, methyl paraben, propyl paraben, benzalconium chloride and benzethonium chloride. Preservatives are typically employed in the range of about 0.1 to 1.0% (w/v).

In some embodiments, the instant nanoparticles are provided in a kit. A kit of the invention is composed of one or more containers, vials, or ready-to-use syringes containing the instant nanoparticles. In one embodiment, a nanoparticle containing a therapeutic agent is provided in a container, vial or syringe. In another embodiment, a nanoparticle containing a prodrug and a nanoparticle containing a prodrug activator are provided in the same container, vial or syringe. In a further embodiment, a nanoparticle containing a prodrug and a nanoparticle containing a prodrug activator are provided in separate containers, vials or syringes. In this respect, the prodrug and activator can be administered at the same time, administered at different times, administered at the same dose and/or administered at different dosages. The nanoparticles can be provided in liquid or lyophilized form, wherein an appropriate solution (e.g. saline solution) can be provided to reconstitute or dilute the nanoparticles. The kit can further include instructions for administration including dosing and rate of administration. Moreover, the instructions can include information concerning the SAR, frequency and relaxation times of the nanoparticles and guidance for using an appropriate frequency for specifically rupturing liposome-encapsulated magnetic nanoparticles bound to target cells.

The compositions and kits of the invention find application in a method for providing a therapeutic agent to a subject in need of treatment, e.g., a subject with cancer. The method involves administering to the subject an effective amount of the carrier-linked magnetic nanoparticles described herein and applying an alternating magnetic field (AMF) to the subject. In one embodiment, the AMF is at a frequency selected for rupturing the liposome carrier that are bound to or associated with target cells (i.e., via the targeting moiety). Given that bound liposomes, liposomes under different viscosities, and liposomes in proximity to macromolecules or cells structures possess different relaxation times, an AMF frequency is selected where the unbound liposomes would have a very low SAR and the bound liposomes or otherwise cell-associated liposomes would have a very high SAR. The AMF refers to a magnetic field that changes the direction of its field vector periodically, typically in a sinusoidal, triangular, rectangular or similar shape pattern, with a frequency in the range of from about 80 kHz to about 800 kHz. The AMF may also be added to a static magnetic field, such that only the AMF component of the resulting magnetic field vector changes direction. It will be appreciated that an alternating magnetic field is accompanied by an alternating electric field and is electromagnetic in nature.

Subjects benefiting from treatment with the instant nanoparticles include, but are not limited to, human or non-human animals with cancer of any type, such as bone marrow, lung, vascular, neuro, colon, ovarian, breast and prostate cancer, diseases of the immune system, such as AIDS and autoimmune conditions, and pathogen-borne diseases, such as HIV, malaria and tuberculosis, and undesirable cell growth, such as adverse angiogenesis, amyloidosis, restenosis, vascular conditions, obesity, toxins and other abnormal cell or tissue growth for which there is a cell surface marker that can be targeted by the instant targeting moiety.

What is claimed is:

1. A method for providing a therapeutic agent to a subject comprising administering to a subject in need thereof a carrier-linked magnetic nanoparticle containing a therapeutic agent and a targeting moiety attached to the carrier-linked magnetic nanoparticle, wherein the carrier is a liposome and the therapeutic agent is encapsulated within the carrier-linked magnetic nanoparticle, and wherein the application of an alternating magnetic field to the subject causes liposomes bound to a target cell in the subject to rupture and release therapeutic agent, while unbound liposomes remain intact, thereby providing the therapeutic agent to the subject.

2. The method of claim 1, wherein the therapeutic agent is a prodrug.

3. The method of claim 1, further comprising administering a carrier-linked magnetic nanoparticle containing a moiety for activating the prodrug.

4. The method of claim 1, wherein the liposome comprises at least one cationic phospholipid or cationic lipid.

5. The method of claim 1, wherein the liposome is modified with polyethylene glycol (PEG).

6. The method of claim 5, wherein the PEG is present in an amount of 0.1% to 30% by weight, based upon the lipid constituting the liposome.

7. The method of claim 6, wherein the PEG is present in an amount of 1% to 15% by weight, based upon the lipid constituting the liposome.

* * * * *